(12) United States Patent
Gieux et al.

(10) Patent No.: US 9,155,372 B2
(45) Date of Patent: Oct. 13, 2015

(54) APPLICATOR FOR A FLUID PRODUCT SUCH AS A COSMETIC PRODUCT

(71) Applicant: AAXEN, Paris (LU)

(72) Inventors: Gerard Gieux, Brussels (BE); Philippe Bonneyrat, Herblay (FR)

(73) Assignee: AAXEN, Paris (FR)

( * ) Notice: Subject to any disclaimer, the term of this patent is extended or adjusted under 35 U.S.C. 154(b) by 0 days.

(21) Appl. No.: 14/282,677

(22) Filed: May 20, 2014

(65) Prior Publication Data

US 2015/0023721 A1 Jan. 22, 2015

Related U.S. Application Data

(63) Continuation of application No. PCT/EP2013/063817, filed on Jul. 1, 2013.

(30) Foreign Application Priority Data

Jul. 2, 2012 (FR) ...................................... 12 56307

(51) Int. Cl.
*A45D 34/04* (2006.01)
*A61M 35/00* (2006.01)

(52) U.S. Cl.
CPC ............ *A45D 34/04* (2013.01); *A45D 2200/10* (2013.01); *A45D 2200/15* (2013.01); *A45D 2200/152* (2013.01); *A61M 35/003* (2013.01)

(58) Field of Classification Search
CPC ........... A45D 2200/10; A45D 2200/15; A45D 2200/152; A45D 2200/155; A45D 2200/1009; A45D 2200/1054; A45D 34/04; A61M 35/00; A61M 35/003
See application file for complete search history.

(56) References Cited

U.S. PATENT DOCUMENTS 7,883,287 B2 * 2/2011 Thorpe .......................... 401/266

FOREIGN PATENT DOCUMENTS

| FR | 2915972 | 11/2008 |
|---|---|---|
| WO | 2011083427 | 7/2011 |

OTHER PUBLICATIONS

International Search Report for PCT/EP2013/063817 published Jan. 9, 2014.

* cited by examiner

*Primary Examiner* — David Walczak
(74) *Attorney, Agent, or Firm* — Brinks Gilson & Lione (57) ABSTRACT

An applicator for a fluid product offers a thermal effect by creating a cold sensation upon application to a surface. The applicator comprises a reservoir containing a fluid product; an end-piece with a dispensing face having an orifice for dispensing the fluid product onto the surface to be treated; and a thermal storage end-piece that includes an application face. The thermal storage end-piece is made from a material having a thermal effusivity that is higher than that of the product dispensing end-piece so as to provide thermal sensations upon contact with the surface to be treated. The application head is shaped so that, by orienting the applicator selectively relative to the surface to be treated, one can place the latter in contact with the dispensing face of the dispensing end-piece while avoiding contact with the application face of the thermal storage end-piece.

12 Claims, 6 Drawing Sheets

APPLICATOR FOR A FLUID PRODUCT SUCH AS A COSMETIC PRODUCT

The present invention relates to an applicator for a fluid product, such as a cosmetic product, for example for application on the skin, the product application and dispensing head of which offers a thermal effect, to create a cold sensation upon application.

by cosmetic product we mean a product as defined in Council Directive 93/35/EEC of 14 Jun. 1993.

It is indeed desirable, in some cases, to associate a thermal sensation with the application of a cosmetic product, particularly in order to enhance the effect thereof.

This is the case in particular for eye contour products for which manufacturers of cosmetic products consider that providing a cold effect on the skin when applying the product allows to reduce wrinkles, remove under-eye bags, attenuate signs of fatigue, firm up or tighten the skin and/or make a person look momentarily younger.

Such benefits are linked to the effect of momentary constriction of blood vessels, resulting in decreased blood flow when the skin comes into contact with a substance providing a cold sensation upon application.

Several devices allowing to dispense a cosmetic product and/or to massage a body surface are known to offer such properties.

The document FR 2 915 972 teaches how to use the thermal effusivity of the materials constituting the applicator for creating a cold sensation upon application.

More particularly, it discloses a dispensing device of a cosmetic product comprising in particular:
- a housing having a reservoir for containing the product;
- a thermal storage end-piece coupled to the housing, the thermal storage end-piece having an application face for applying the product on a surface and,
- an insert disposed in the thermal storage end-piece, the insert defining a passageway for dispensing the product in communication with the reservoir, the product dispensing passageway extending through the thermal storage end-piece and ending with an opening in the application face.

By thermal storage end-piece we mean an end-piece made of a material, the thermal effusivity of which is much higher than that of the area treated by the corresponding applicator.

Thermal Effusivity is the capacity of a material to absorb calories.

The more its value is high, the more the material is adapted to absorb calories without overheating and conversely.

The intrinsic value of the Thermal Effusivity of a material is calculated in the following manner:

$$Ef = \sqrt{k.\rho.c}$$

where
K is the thermal capacity in $W.m^{-1}.°K^{-1}$; $\rho$ is the density in $kg/m^3$; c is the thermal conductivity in $J.kg^{-1}.°K^{-1}$.

Thus, upon contact with the skin, while all parts are at the same temperature, a part made of steel (Effusivity of which is in the order of 14000 $J.K^{-1}.m^{-2}.s^{-1/2}$) will provide a cold sensation on the skin (Effusivity of 400 $J.K^{-1}.m^{-2}.s^{-1/2}$), while a part made of wood (Effusivity likewise in the order of 400 $J.K^{-1}.m^{-2}.s^{-1/2}$) will provide a neutral sensation.

This heat transfer provides a cold sensation on the skin which intensifies as the Thermal Effusivity increases.

Yet, such devices have numerous drawbacks.

Firstly, it is not possible for the user to avoid the cold sensation that the applicator contact provides to its skin when using the corresponding product dispensing device.

Yet, this cold sensation is not often necessary or desired each time the product dispensing device is used. The user may want to enjoy only the cosmetic product, without necessarily undergoing an ice-cold contact which can be unpleasant in some circumstances.

In addition, to provide a cold sensation that is not too transient, a large enough surface with high thermal effusivity is needed; hence the tendency to increase the envelope surface of the application face of the thermal storage end-piece.

Yet, the product dispensing being carried out via an aperture opening into this application face, an excessively large surface impairs the precision of the product dispensing, particularly on sensitive parts of the eye contour type.

Such devices are often unsuitable for dispensing a cosmetic product on complex non-flat surfaces, with both concavities and convexities such as the eye contour, this application having to be very precise to avoid any risk of eye irritation from the cosmetic product.

Furthermore, because of inaccuracies in dispensing the product, the user tends to dispense and use a greater quantity of the product contained in the reservoir.

There is a need for greater precision in the choice of the sensation provided by the application and/or in the dispensing and the application of a cosmetic product on an area to be treated.

Thus, an object of the present invention is to propose an applicator in which choosing whether or not to benefit from the cooling properties of the applicator is left to the user.

It is also desirable to propose an applicator in which the dispensing of the product on the area to be treated is controlled, in order to enhance the precision in the dispensing zone and the quantity of the dispensed product.

To this end, the invention proposes an applicator for a fluid product such as a liquid, semi liquid or viscous product comprising a reservoir containing the product and an application head, coupled to the reservoir, comprising:
- an end-piece for dispensing the product in communication with the reservoir including a face for dispensing the product on a surface to be treated such as a user's skin, this end-piece defining a path for dispensing said product, in communication with the reservoir, the path for dispensing the product extending through the dispensing end-piece and ending with an orifice on the dispensing face, adapted to dispense the product on the surface to be treated,
- a thermal storage end-piece including an application face on the surface to treated.

The applicator is remarkable in that:
- the thermal storage end-piece (200) is made of a material, the thermal effusivity of which is higher than that of the dispensing end-piece (100) so as to provide two different thermal sensations upon contact with the surface to be treated and,
- the application head is shaped so that, by orienting the applicator selectively relative to the surface to be treated, a user can place the latter in contact with the dispensing face of the dispensing end-piece while avoiding contact with the application face of the thermal storage end-piece.

According to particular embodiments of the invention, a fluid product applicator according to the invention may comprise one or more of the following characteristics, taken in isolation or in technically possible combination:
- the respective dispensing and application faces of the dispensing end-piece and the thermal storage end-piece are defined by respective envelope surfaces not included in each other and disjoined;

the application face is offset relative to the dispensing face along a longitudinal axis of the applicator and/or angularly around the periphery of said applicator;

a break in slope and/or discontinuity are arranged between the dispensing and application faces;

the thermal storage end-piece and the dispensing end-piece form two complementary areas of the outer contour of the applicator over at least a portion of the length thereof;

the thermal storage end-piece extends over a first portion of the outer peripheral contour of the applicator and the dispensing end-piece extends over a second portion of the peripheral contour of the applicator, complementarily to the thermal storage end-piece;

the dispensing end-piece is shaped like an elongated cannula ending with the dispensing orifice;

the dispensing orifice is offset to the outer periphery of the application face of the thermal storage end-piece and/or protruding from the application head;

the thermal storage end-piece is formed by a ring with a domed application face, adapted to be removably mounted on the dispensing end-piece.

Other features, objects and advantages of the present invention will become apparent upon reading the following detailed description, according to embodiments given by way of non-limiting examples, and with reference to the accompanying drawings wherein.

Referring now to FIGS. 1a to 1d, representing an applicator 10 for a fluid product such as a liquid, semi liquid or viscous product contained in a container 20 or reservoir and intended to be applied by means of an application head 40 coupled to one end of the reservoir 20. This applicator 10 extends longitudinally along a longitudinal X-axis.

Where appropriate, the application head 40 cooperates with a closing hood 30 of the applicator 10, not shown in these figures. It will be described in more detail below.

More particularly, this applicator 10 comprises an application head 40 formed by:

an end-piece 100 called product dispensing end-piece in communication with the reservoir 20, comprising an active dispensing face 110 of the product on a user's surface to be treated such as a skin This end-piece 100 defines a dispensing passageway 120 of said product in communication with the reservoir 20, the product dispensing passageway 120 extending through the dispensing end-piece 100 and ending with an opening 121 on the dispensing face 110, adapted to dispense the product on the surface to be treated;

an end-piece 200 called thermal storage end-piece, comprising an active application face 210 on the surface to be treated.

By "active face" 110, 210 we mean the surface of each end-piece 100, 200 intended to be applied on the user's surface to be treated, as part of use of the applicator 10 in accordance with intended purpose thereof.

The dispensing end-piece 100 and, more particularly, the dispensing face 110, is made of a material, thermal effusivity of which is close to that of the user's surface to be treated, providing therefore the user with a neutral sensation.

The thermal storage end-piece 200 and, more particularly, the application face 210, is made of a material with high thermal effusivity compared to that of the user's surface to be treated.

The thermal effusivity of the active application face 210 of the thermal storage end-piece 200 is therefore higher than that of the active application face 110 of the product dispensing end-piece 100.

In addition, the application face 210 is adapted to perform, if necessary, a massage on the treated area.

Advantageously, the application head 40 is shaped so that, by orienting the applicator 10 selectively relative to the surface to be treated, a user can place the latter in contact with the dispensing face 110 of the dispensing end-piece 100 while avoiding contact with the application face 210 of the thermal storage end-piece 200.

Thus, the dispensing 100 and thermal storage end-pieces 200 are both shaped so that, when applying the applicator 20 on a flat surface of the user's skin, the active dispensing face 110 may dispense and apply the product on the treated surface, without the treated surface coming in contact simultaneously with the application face 210 of the thermal storage end-piece 200 likely to provide a cold sensation to said surface.

Therefore, a voluntarily manipulation of the hand should be performed to turn the applicator 10 in order to change the orientation thereof relative to the treated skin area and voluntarily enjoy the thermal effect on this area.

In this context, unlike the prior art considered, the respective active dispensing 110 and application 201 faces of the dispensing 100 and thermal storage 200 end-pieces are defined by respective envelope surfaces not included in each other and disjoined.

By envelope surface we mean the entire active surface area of the application face considered, intended to be applied on the user's surface to be treated as part of use of the applicator 10 in accordance with intended purpose thereof.

Each dispensing 100 and thermal storage 200 end-piece can have any shape that complies with the above applicator 10 properties.

The relative configurations of the two dispensing 110 and application 210 faces of the two end-pieces 100, 200 may be not included in each other and disjoined in a variety of ways.

A break in slope, a discontinuity, an axial or angular offset may, in particular, be provided between or on either one of the two considered active faces 110, 210 or considered envelope surfaces.

More particularly, the application face 210 of the thermal storage end-piece 200 is offset relative to the dispensing face 110 of the dispensing end-piece 100 along the X-axis of the applicator 10 and/or angularly around the periphery of said applicator 10.

Thus, the user places the surface to be treated in contact in a selective manner:

either with the dispensing face 110 of the dispensing end-piece 100, in order to dispense and apply the product on the treated surface, avoiding any cold sensation during the dispensing and the initial application of the product;

or with the application face 210 of the thermal storage end-piece 200, where appropriate, if he/she wishes to enjoy a cold sensation, after the dispensing and the initial application of the product on the treated surface.

The shape of each end-piece 100, 200 and, more particularly, the characteristics of each of the dispensing 110 and application 210 faces may be different depending on the product to be applied or the type of application.

Each may, in particular but not exclusively, be spherical, curvilinear, parabolic, flat, convex, ogival or constitute a combination of known forms.

Different alternative embodiments of dispensing 100 and thermal storage 200 end-pieces are shown in FIGS. 1 to 8.

With reference to FIGS. 1 to 7, applicators 20 can be seen wherein, in a sectional view of the applicator 10, the thermal storage end-piece 200 and the dispensing end-piece 100 form two complementary areas of the outer contour of the applicator 10 over at least a portion of the length thereof.

In these figures, the thermal storage end-piece 200 extends over a first portion of the peripheral contour of the applicator 20 and the dispensing end-piece 100 extends over a second portion of the peripheral contour of the applicator 10, complementarily to the thermal storage end-piece 200.

More particularly, with reference to FIGS. 1a to 1d, in a first alternative embodiment, the application head 40 has an envelope surface shaped like a paraboloid beveled at its upper end.

The bevel coincides with the product dispensing face 110 and forms an inclined plane relative to the X-axis of the applicator 10.

The product passageway 120 from the reservoir 20 to the dispensing face 110 is arranged with a dispensing channel 122 of the end-piece 100 extending along the X-axis and opening into the orifice 121 arranged on the upper part of the beveled face 110.

The beveled dispensing face 110 defines a substantially flat application surface which allows to apply the product on the surface to be treated.

Furthermore, the dispensing channel 122 can be in the form of one or more tubular member(s) in communication with one or more reservoir(s) 20.

It may also be in the form of a constant or non-constant section and even be adapted to open into several orifices 121 on the beveled face 110 of the end-piece 100.

As to the thermal storage end-piece 200, it is shaped like the complementary fraction of that of the dispensing end-piece 100.

In a sectional view of the applicator 10, over a portion of the length of the application head 40, the thermal storage end-piece 200 has a C-shaped section cooperating with a section having a complementary shape of the dispensing end-piece 100.

This thermal storage end-piece 200 is provided with an open longitudinal groove 220, the concavity of which is oriented toward the channel 122 of the dispensing end-piece 100 and the shape and dimensions of which are adapted to receive this channel 122.

The upper end 201 of the thermal storage end-piece 200 opposite the reservoir 20 is, for its part, shaped to match to an inner face of the beveled dispensing face 110 on a portion of the outer periphery thereof.

Thus, the active application face 210 of the thermal storage end-piece 200 is formed by the curved outer surface of the end-piece 200.

The active dispensing face 110 is accordingly separated from the active application face 210 by a curved ridge.

It is, therefore, necessary to make a rotation around an axis inclined relative to the X-axis to switch from the dispensing and the initial application of the product on the user's skin to application/massage of the product, providing a cold sensation on the user's skin when using the applicator 20.

Figures 1A, 1B, 1C, 1D:
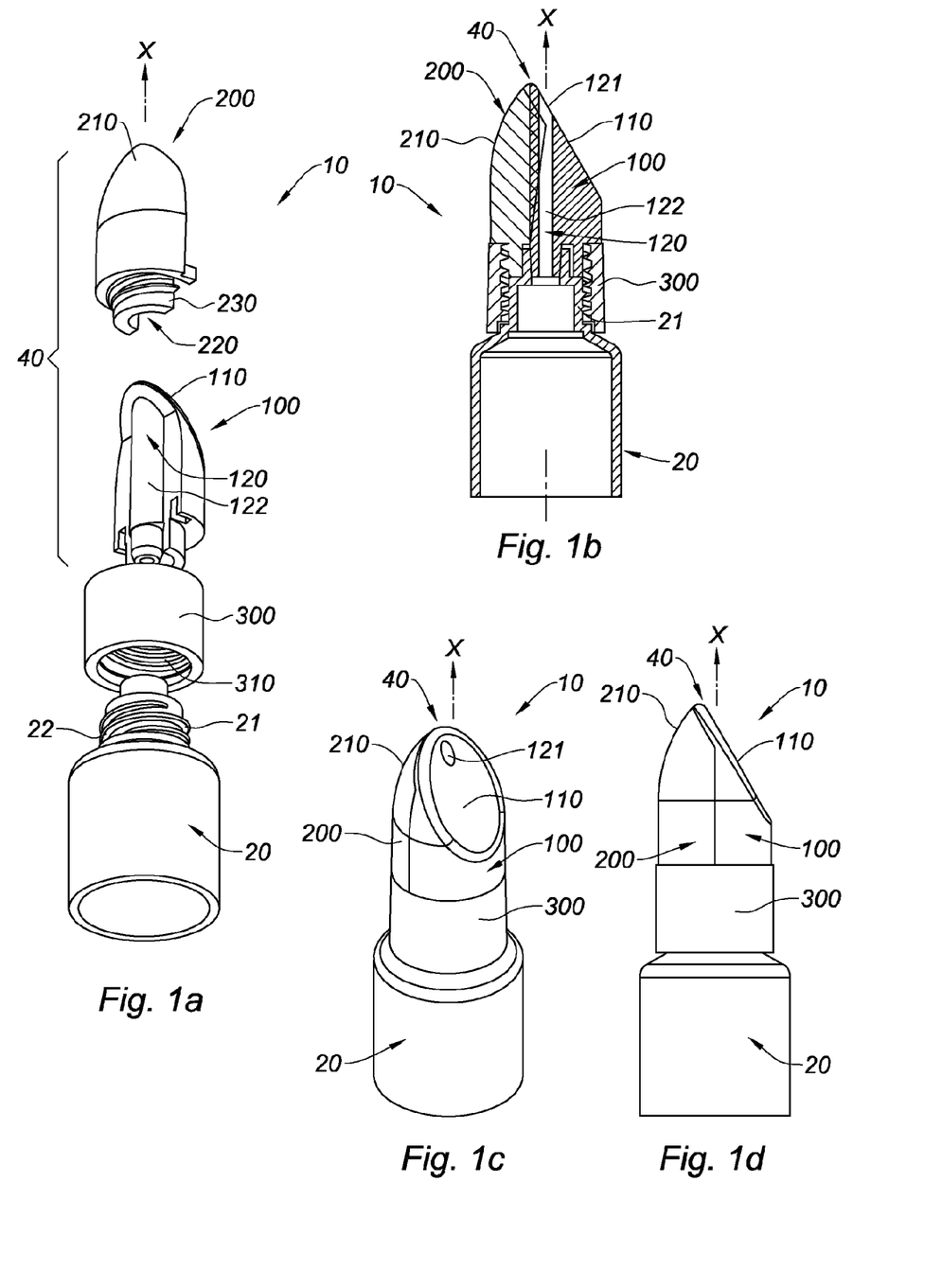
FIGS. 1a, 1b, 1c, 1d are, respectively, exploded perspective, longitudinal sectional, perspective and side views of a first embodiment of an applicator according to the present invention.
Figure 2A:
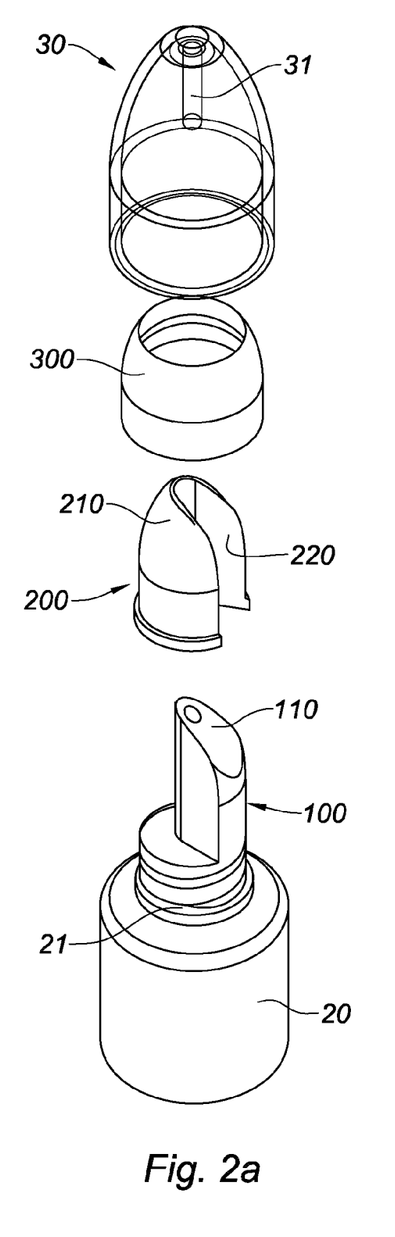
FIGS. 2a, 2b, 2c are, respectively, exploded perspective, side and perspective views of a second embodiment of an applicator according to the present invention.
Figure 2B:
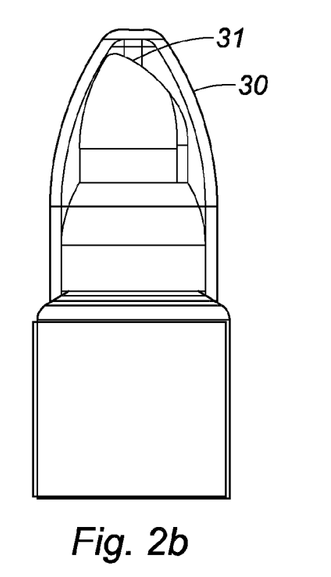
Figure 2C:
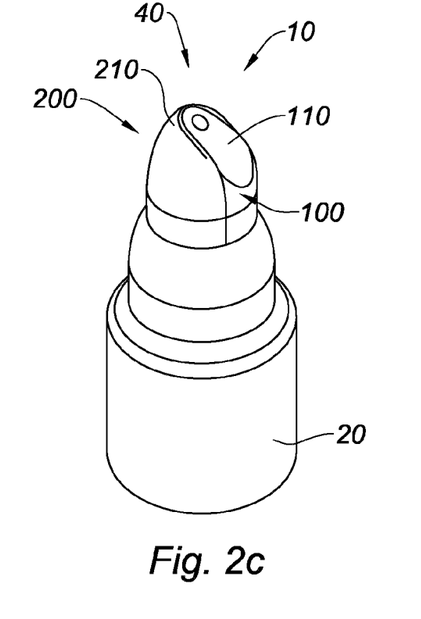

In the alternative embodiment shown in FIGS. 2a to 2c, the dispensing 100 and thermal storage 200 end-pieces are identical to those described in FIGS. 1a to 1d, barring the following differences.

The dispensing end-piece 100 has a rounded triangular cross-section at the tops.

The thermal storage end-piece 200 has, for its part, a cross section complementary to that of the dispensing end-piece 100. The shape and dimensions of the longitudinal groove 220 are, thus, adapted to receive the dispensing end-piece 100.

The bevel of the application head 40 is of a triangular section, formed solely by the active dispensing face 110 of the dispensing end-piece 100.

Similarly to FIG. 1, the dispensing orifice 121 is arranged in the upper portion of the dispensing face 110.

To isolate the active dispensing face 110 from the outer surface of the end-piece, this dispensing face 110 is shaped to surmount the outer surface of the thermal storage end-piece 200.

As a consequence, there is a break in slope between the dispensing face 110 and the corresponding outer periphery of the thermal storage end-piece 200 which forms, with the rest of the outer surface of the end-piece, the active application face 210.

The absence of contact with the material upon a cold contact is thus ensured during the initial application of the product on the treated area.

With reference to FIGS. 3a to 3d, the application head 40 has a generally cylindrical shape, the upper end of which, intended to be oriented opposite the reservoir 2 (not shown in these figures), assumes the shape of a bevel.

The dispensing end-piece 100 is shaped like an elongated cannula 130 ending, at its end opposite the reservoir 20, with the dispensing orifice 121.

The dispensing face 110 is accordingly reduced to the dispensing orifice 121.

Such reduction in the dispensing face, just like the offset of the dispensing orifice 121 to the outer periphery of the application face 210 and/or protruding from the application head 40 allows, advantageously, to improve the dispensing accuracy of the product on the surface to be treated, especially in complex areas of the face such as the eye contour.

Risks of infection to the sensitive areas to be treated by the product are thus minimized.

In addition, a precise dispensing of the product leads to a quantity saving of the product to be dispensed. Excessive dispensing of the product is brought under control.

The thermal storage end-piece 200 partially surrounds this cannula 130 and houses it into the open longitudinal groove 220 with adapted shape and dimensions.

In addition, this end-piece 200 has a beveled application face 210 of circular section, forming a plane inclined relative to the X-axis.

The dispensing orifice 121 is arranged at the outer periphery of this application face 210, axially offset along the X-axis at a slightly higher altitude to form a tip of the applicator 20.

The dispensing orifice 121 is further inclined in a symmetrical direction relative to a plane that is longitudinal to that of the beveled application face 210.

It is angularly offset around the X-axis of the application face 210.

Thus, the active dispensing face 110 is disjoined from the application face 210 of the thermal storage end-piece 200.

Figure 3A:
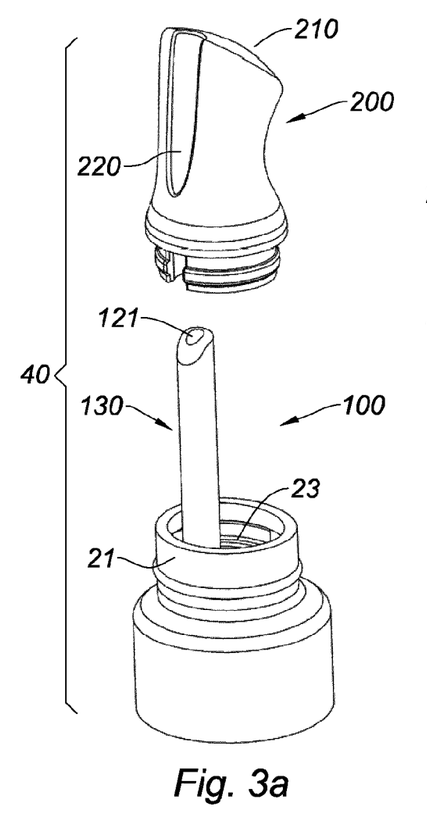
FIGS. 3a, 3b, 3c, 3d are partial, respectively, exploded perspective, longitudinal sectional, perspective and side views of a third embodiment of an applicator according to the present invention.
Figures 4A, 4B, 4C, 5A, 5B:
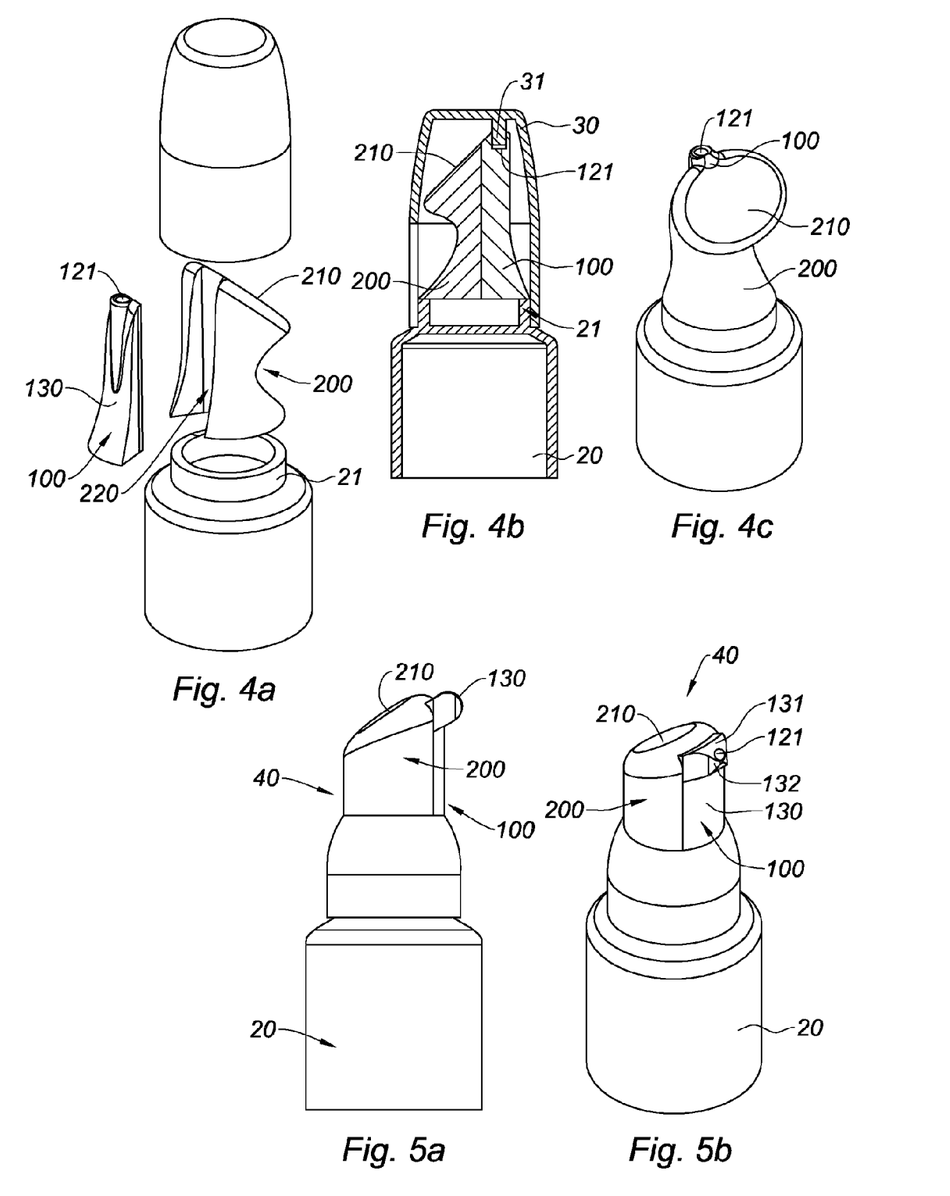
FIGS. 4a, 4b, 4c are, respectively, exploded perspective, side and perspective views of a fourth embodiment of an applicator according to the present invention.
FIGS. 5a and 5b are, respectively, side and perspective views of a fifth embodiment of an applicator according to the present invention.

The application head 40 of the alternative embodiment shown in FIGS. 4a to 4c differs from the one shown in FIG. 3 in that the dispensing orifice 121 is not inclined but shaped like a flat surface perpendicular to the X-axis.

The disjoined property of the dispensing face 110 relative to the application face 210 of the thermal storage end-piece 200 is ensured by an axial offset along the X-axis of the dispensing orifice 121 relative to the outer contour of the application face 210.

The dispensing orifice 121 protrudes axially to the outer periphery of the application face 210 where it is offset and forms a side tip of the applicator 10.

In addition, the cannula 130 is separate from the reservoir 20 while in FIG. 4, the cannula 130 forms an extension of the reservoir 20.

Such an alternative embodiment of an application head 40 allows also to promote a more precise dispensing of the product on the user's treated areas.

This is also the case for the alternative embodiment shown in FIGS. 5a and 5b which differs from the alternative embodiment of FIG. 3 in that the cannula 130 of the dispensing end-piece 100 is bent.

The upper branch 131 of the cannula 130 is directed in a direction opposite to that of the application face 210 of the thermal storage end-piece 200.

The cannula 130 is thus shaped such that the dispensing orifice 121 protrudes laterally from the application head 40, to the upper outer periphery of the application face 210 of the thermal storage end-piece 200.

In a non-limiting example shown in this alternative, the free end of this cannula 130 assumes the shape of a pyramid 132 in which the dispensing orifice 121 is arranged.

Figure 6A:
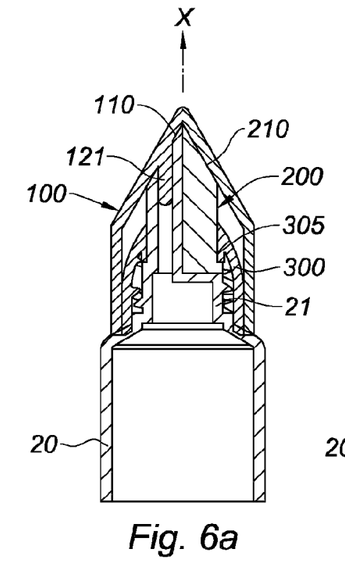
FIGS. 6a, 6b, 6c are, respectively, longitudinal sectional and two side views of a sixth embodiment of an applicator according to the present invention.
Figures 6B, 6C:
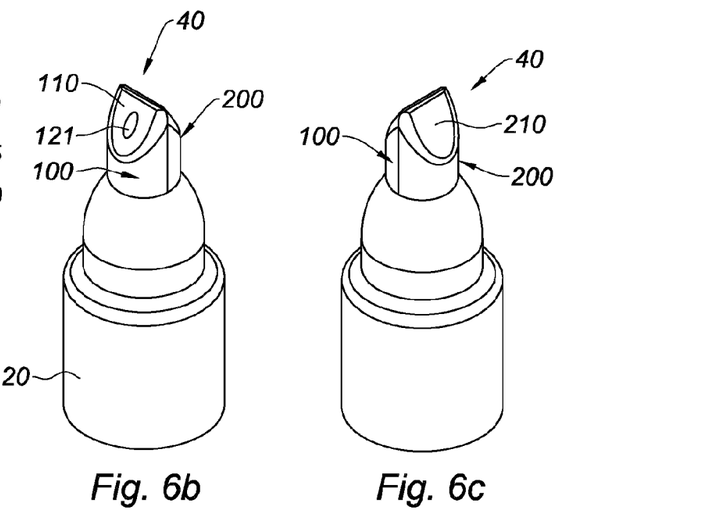

With reference to FIGS. 6a to 6c, the application head 40 is formed by a dispensing end-piece 100 and a thermal storage end-piece 200 disposed on either side of a symmetrical median longitudinal plane.

The two dispensing 100 and thermal storage 200 end-pieces have, respectively, dispensing 110 and application 210 faces in the form of bevels oriented in two different directions and separated by an upper end ridge.

Each end-piece 100, 200 has, in cross-section, a complementary semicircle section.

The double bevel allows to avoid any cold contact during the dispensing and initial application of the product on the user's skin.

To provide a cold sensation, it is suitable to rotate the applicator by 180° around the X-axis.

Figures 7A, 7B:
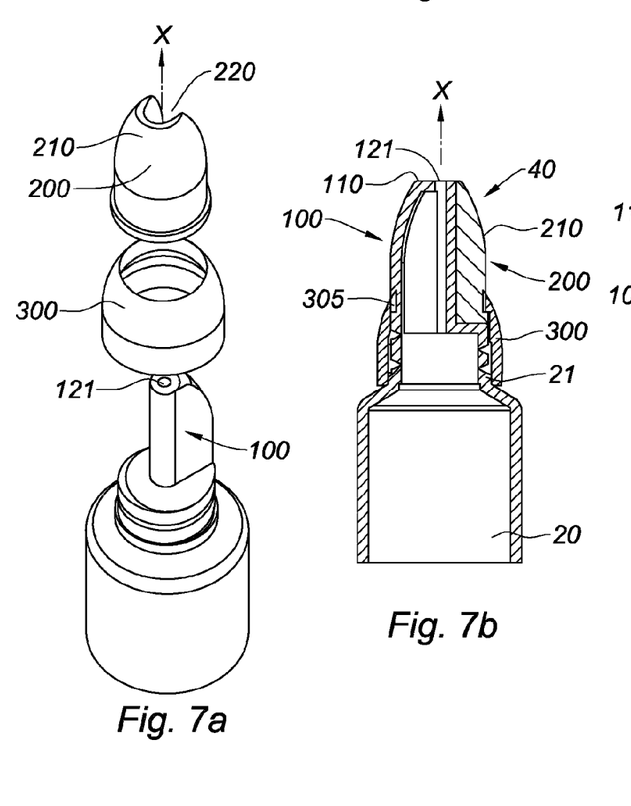
FIGS. 7a, 7b, 7c are, respectively, exploded perspective, longitudinal sectional and perspective views of a seventh embodiment of an applicator according to the present invention.
Figure 7C:
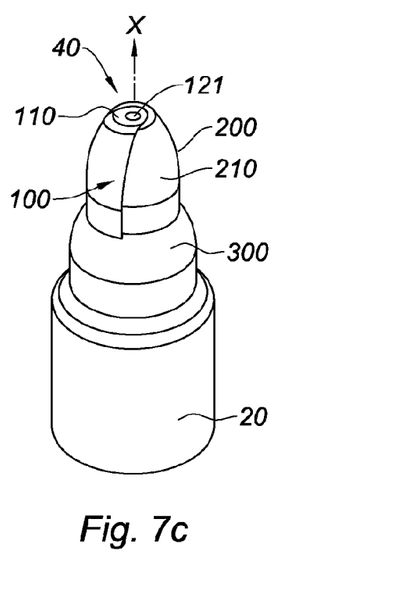

With reference to FIGS. 7a to 7c, the application head 40 has two complementary end-pieces 100, 200 shaped to give the head 40 a general truncated ogive shape, at its upper end, along a plane perpendicular to the X-axis.

This ogive 40 has a circular cross section.

The dispensing end-piece 100 is, for its part, of triangular cross section, with a rounded top.

The dispensing face 110 coincides with the truncated plane of the applicator 20.

The dispensing orifice 121 opens into this dispensing face 110 at the top of the applicator 20.

regarding the thermal storage end-piece 200, it has an active application face 210 defined by the outer circumference of the ogive area it forms.

The application 210 and dispensing 110 faces are not included in each other and are severed by the presence of a break of slope and an axial and angular offset along the X-axis.

Thus, to receive a cold sensation after a dispensing and an initial application of product on a treated area, it is necessary to rotate the applicator 10 along an axis perpendicular to the X-axis.

Figure 8A:
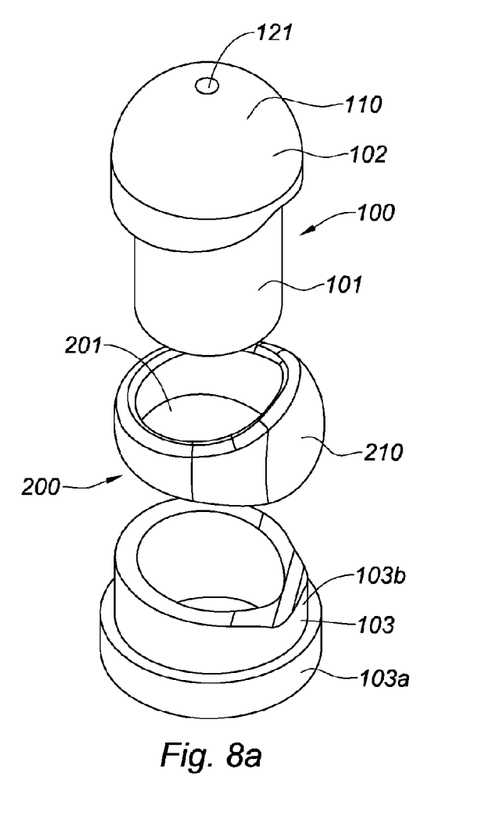
FIGS. 8a, 8b, 8c are partial, respectively, exploded perspective, perspective and side views of an eighth embodiment of an applicator according to the present invention.
Figure 8B:
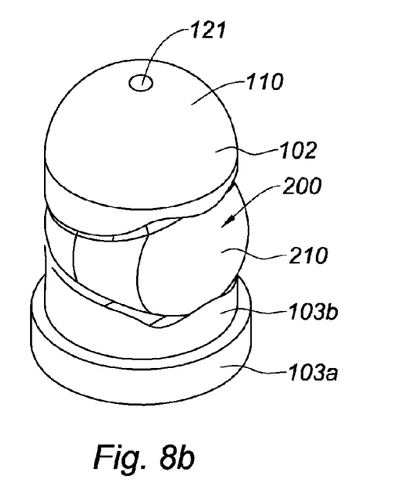
Figure 8C:
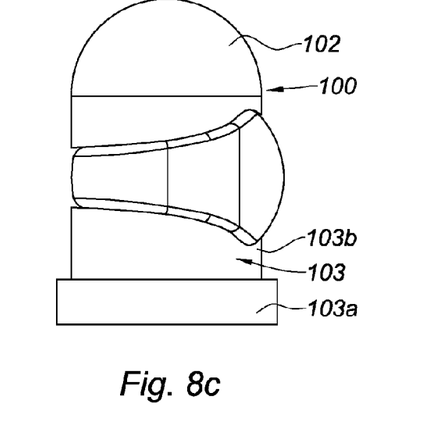

A complementary alternative embodiment is shown in FIGS. 8a to 8c.

In this alternative embodiment, the dispensing end-piece 100 assumes the shape of two distinct elements, namely a first tubular element 101 extended at its upper end of a spherical cap 102 and a first cylinder 103a extended by a second cylinder 103b with a reduced diameter, the double cylinder 103 being open at each end.

The dispensing channel 122 is arranged within the tubular element 101 and opens into an orifice 121 at the top of the spherical cap 101.

In this context, the active dispensing face of 110 is defined by the outer surface of the spherical cap 101.

regarding the thermal storage end-piece 200, it comprises a ring provided on a portion of the circumference thereof with a doomed surface defining the thermal application face 210.

This ring is interposed between the two elements 101, 103 constituting the dispensing end-piece 100.

The tubular element 101 of the dispensing end-piece 100 is removably mounted in a central through orifice 201 of this ring.

The ring is therefore mounted at the outer periphery of the tubular element 101 under the spherical cap 201.

The two dispensing 110 and application 210 faces are thus angularly offset, without limitation, in the order of 90 degrees, which allow to initially apply the product on a treated area without feeling any cold sensation.

The shape of the thermal storage end-piece 200 advantageously allows the user to wear the end-piece 200 like a ring either as a jewel or for easier massage of a particular area of skin.

Moreover, the dispensing end-piece 100 is made from an inert material from a chemical point of view regarding the skin or the product contained in the container 20 and from a thermal point of view by providing a neutral sensation upon contact with the user's treated area.

Such a material can be, without limitation, a plastic material.

In non-limiting examples of the present invention, it can be made from a material selected from the following group: high and low density polyethylene (HDPE or LDPE), polypropylene (PP), Polyethylene terephthalate (PET), polystyrene (PS), acrylonytrile butadiene styrene (ABS), styrene acrylonitryle (SAN), Polyacetal (POM), SEBS Poly(Styrene-Ethylene-Butadiene-Styrene), ethylene-propylene-diene monomer EPDM, rubber, silicone, thermoplastic elastomers, or any other flexible plastic material.

Regarding the thermal storage end-piece 200, it is made of a material which allows to ensure the cold effect upon application related to the thermal effusivity of the material.

In non-limiting examples of the present invention, it can be made from a material selected from the following group: metallic materials (steel, copper, aluminum, titanium), ceramic materials, metal oxides (aluminum oxide or alumina, zirconium oxide or zyrcone), or other technical ceramics, glass, composite materials, mineral material, such as marble.

It can also be any piece of material covered with a material with high thermal effusivity such as metal coating using a galvanizing metalizing anodizing process or by an enamel-coating.

Moreover, the thermal storage end-piece 200 can be solid or surface-covered with a film or a coating made of such a material, and even partially made from such a material.

Furthermore, in order to extend to the maximum cold contact on the treated area, the dispensing 100 and thermal storage 200 end-pieces and, more particularly, the envelope surfaces of the dispensing 110 and application 210 faces occupy minimum and maximum volumes, respectively.

Furthermore, with reference to FIGS. 1 and 4 to 7, the reservoir 20 may be of any known type.

It may thus be made of a rigid or flexible tube.

The applicator 10 may further comprise a product dispensing mechanism (not shown) for dispensing the product by the applicator 10, the product dispensing mechanism comprising a ratchet movement, tube compression, aerosol or piston dispensing mechanism.

In addition, the container 20 may or may not include a neck 21 reduced relative to the dimensions of the container 20, in the form of an open cylindrical skirt.

This neck 21 cooperates with the application head 40 to ensure mounting of the head on the reservoir 20 and fluid communication between the reservoir 20 and the dispensing channel 122 of the dispensing end-piece 100.

This neck 21 may be integrally formed with the reservoir 20 or attached to the latter.

Regarding the mounting of the application head 40 on the body of the reservoir 20, several alternative embodiments are shown in FIGS. 1 to 4 and 6 to 7.

Thus, each dispensing end-piece 100 and each thermal storage end-piece 200 may be mounted on the body of the container 20 by snapping, bonding, crimping, clamping, screwing, ribbing or retaining barbs on the interior of each thermal storage 200 and/or dispensing 100 end-piece and/or on the exterior of the neck 21 and/or by one-piece molding and/or by means of a fastening ring 300 or by any other appropriate fastening means.

With reference to the alternative embodiment of FIG. 1, the dispensing end-piece 100 is fixedly mounted by elastic clamping of the dispensing channel 122, well-shaped, in the neck 21.

In addition, the fastening system proposes a fastening ring 300 with a threading 310 complementary, on the one hand, to an outer threading arranged on a skirt 230 of the thermal storage end-piece 200 intended to be mounted to the outer periphery of the neck 21 and, on the other hand, to an outer threading 22 of the neck 21.

With reference to the alternative embodiment of FIG. 2, the dispensing end-piece 100 is integrally molded with the reservoir 20.

This allows to overcome the problems of sealing between the two parts and also to make manufacturing and tooling savings.

The thermal storage end-piece 200 is, for its part, held onto the neck 21 by an adapted fastening ring 300, configured to be mounted to move helicoidally on the outer periphery of the neck 21 by complementary threadings arranged on the neck 21 and the ring 300.

The alternative embodiment of FIG. 3 differs from the alternative embodiment of FIG. 2 in that the thermal storage end-piece 200 is shaped to be inserted into a closed recess 23, with a complementary shape, of the neck 21.

It is further held by a fastening ring 300 mounted adjusted on the periphery of the neck 21 so as to prevent any movement in translation of the thermal storage end-piece 200.

In FIG. 4, the thermal storage 200 and dispensing 100 end-pieces are bonded to the reservoir 20.

In both alternative embodiments shown in FIGS. 6 and 7, each end-piece 100, 200 is held by a fastening ring 300 mounted on the outer periphery of the neck 21 by complementary threadings so as to prevent any movement in translation of the end-pieces 100, 200.

It comprises an inner cylindrical skirt 305 adapted to form a stop with an outer shoulder arranged to the periphery of each end-piece 100, 200 at their end opposite the reservoir 20.

Alternatively, the fastening of the ring 300 can be achieved by snapping or by cooperation of one or several slots adapted to cooperate with complementary spurs.

The applicator 10 must also have an optimal sealing.

In this context, various sealing means may be proposed in combination or not.

Mention may be made, in particular, of particular configurations of the dispensing channel 122 and the orifice of the neck 21 of the reservoir 20 adapted to cooperate sealingly so that the product cannot exit under the pressure effect.

Sealing gaskets (not shown in the figures) can be provided between the reservoir 20 and the dispensing end-piece 100.

This includes providing a gasket with a shape conforming to or pressing against a cooperating shape of the reservoir 20 or a gasket enclosing the dispensing end-piece 100 appropriately to ensure sealing with the outlet of the reservoir 20.

Complementarily, means for closing the product supply channel(s) 122 in case of non-use of the applicator 20 may also be provided.

In particular, a control ring may be implemented, movably mounted on the reservoir between a closed position where it closes the orifice of the outlet of the reservoir 20 and an open position where it clears the orifice of the outlet of the latter by rotation, traction or any other opening/closing system.

As previously indicated, a closing cap 30 configured to cap applicator 20 may also be provided.

This cap 30 may have any desired shape.

It is adapted to be movably mounted, by screwing, ratcheting, snapping or by any other suitable fastening means on the reservoir 20 and/or the application head 40, so as to be easily removed and replaced by the user while ensuring a sealed closure of the applicator, where appropriate.

Figure 3B:
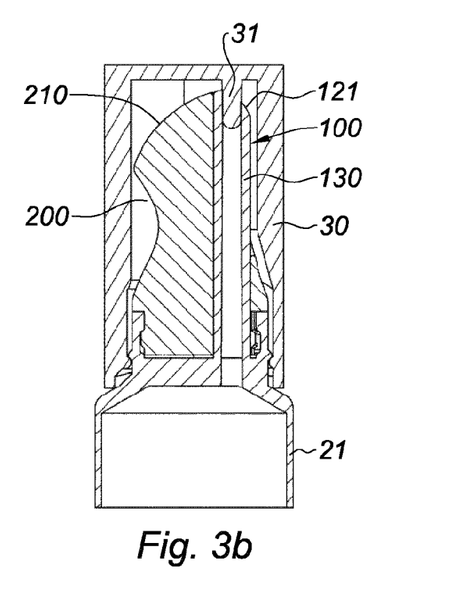
Figure 3C:
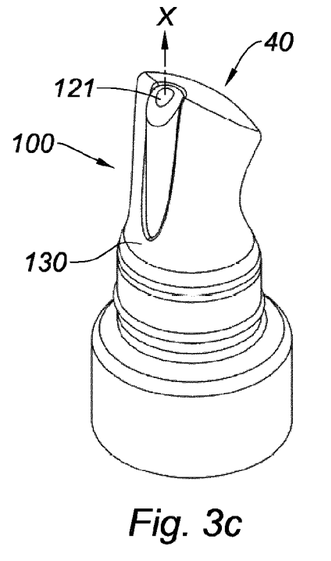
Figure 3D:
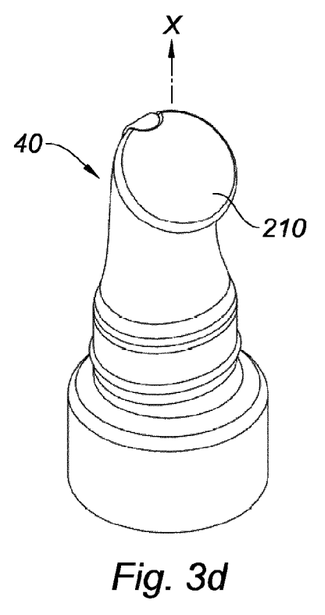

Such closing caps 30 are shown as examples in FIGS. 2a and 3b.

With reference to these figures, it can be seen that the closing cap 30 may comprise a shutter pin 31 adapted to seal the orifice 121 opening into the dispensing face 110 of the dispensing end-piece 100.

This pin 31, of cylindrical shape, penetrates into the orifice 121 in order to maintain sealing.

Product losses when the applicator 20 is not used are, therefore, avoided.

Of course, the applicator 10 can contain any type of liquid, semi-liquid or viscous fluid product.

These include, particularly but not exclusively, cosmetic products, eye contour care, concealer, medical products, makeup (including lipstick), hair care or hair dyes.

Of course, the invention is not limited to the examples which have just been described, and many arrangements can be provided to these examples without departing from the scope of the invention.

It is thus to be noted that in all alternative embodiments described, the application 120 and dispensing 110 faces with smooth surfaces may be replaced or supplemented with rougher surfaces or by a foam, felt or brush type coating.

Moreover, roll-type mobile application elements, vibrating elements, electrodes or any other element adapted to stimulate the treated areas and/or improve the penetration or effectiveness of the applied product may be arranged on the application head 40

The invention claimed is:

1. An applicator (10) for a fluid product such as a cosmetic product, comprising a reservoir (20) adapted to contain the product and an application head (40), coupled to the reservoir (20), the application head comprised of:
   an end-piece (100) for dispensing the product in communication with the reservoir (20) including a face (110) for dispensing the product on a surface to be treated such as a user's skin, this end-piece (100) defining a path for dispensing said product in communication with the reservoir (20), the product dispensing path extending through the dispensing end-piece (100) and ending with an orifice (121) on the dispensing face (110), adapted to dispense the product on the surface to be treated, and
   a thermal storage end-piece (200) including an application face (210) for contacting the surface to be treated,
   the applicator (10) being characterized in that:
   the thermal storage end-piece (200) is made from a material, thermal effusivity of which higher than that of the product dispensing end-piece (100) so as to provide two different thermal sensations upon contact with the surface to be treated and,
   the application head (40) is shaped so that, the application face (210) does not completely encompass the dispensing face (110) and by orienting the applicator (10) selectively relative to the surface to be treated, a user can place the surface to be treated in contact with the dispensing face (110) of the dispensing end-piece (100) while avoiding contact with the application face (210) of the thermal storage end-piece (200).

2. The applicator according to claim 1 wherein the respective dispensing (110) and application (210) faces of the dispensing end-piece (100) and the thermal storage end-piece (200) are defined by respective envelope surfaces not included in each other and disjoined.

3. The applicator according to claim 2 wherein the active application face (210) is offset relative to the dispensing face (110) along a longitudinal axis of the applicator (10) and angularly around the periphery of said applicator (10).

4. The applicator according to claim 2 wherein a break in slope and a discontinuity is arranged between the dispensing and application faces.

5. The applicator according to claim 2 wherein the application face (210) is offset relative to the dispensing face (110) along a longitudinal axis of the applicator (10) or angularly around the periphery of said applicator (10).

6. The applicator according to claim 2 wherein a break in slope or a discontinuity is arranged between the dispensing and application faces.

7. The applicator according to claim 1 wherein the thermal storage end-piece (200) and the dispensing end-piece (100) form two complementary areas of an outer contour of the applicator (10) on at least a portion of the length of the applicator (10).

8. The applicator according to claim 7 wherein the applicator has an outer peripheral contour; the thermal storage end-piece (200) extending over a first portion of the outer peripheral contour of the applicator (10) and the dispensing end-piece (100) extending over a second portion of the peripheral contour of the applicator (10), complementarily to the thermal storage end-piece (200).

9. The applicator according to claim 8 wherein the dispensing orifice (121) is offset to the outer periphery of the application face of the thermal storage end-piece and protruding from the application head.

10. The applicator according to claim 8 wherein the dispensing end-piece (100) is shaped like an elongated cannula (130) ending with the dispensing orifice (121).

11. The applicator according to claim 8 wherein the dispensing orifice (121) is offset to the outer periphery of the application face of the thermal storage end-piece or protruding from the application head.

12. The applicator according to claim 1 wherein the thermal storage end-piece (200) is formed by a ring provided with a domed application face, adapted to be removably mounted on the dispensing end-piece.

* * * * *